(12) United States Patent
Hajjiah et al.

(10) Patent No.: US 10,441,211 B1
(45) Date of Patent: Oct. 15, 2019

(54) METHOD OF DETECTING BONE FRACTURES USING BACKSCATTERED LIGHT

(71) Applicants: Ali Hajjiah, Safat (KW); Ebraheem Sultan, Safat (KW); Kawther Al Mejadi, Safat (KW); Sara Al Omran, Safat (KW); Shemoukh Al Failakawi, Safat (KW); Sara Borjaib, Safat (KW)

(72) Inventors: Ali Hajjiah, Safat (KW); Ebraheem Sultan, Safat (KW); Kawther Al Mejadi, Safat (KW); Sara Al Omran, Safat (KW); Shemoukh Al Failakawi, Safat (KW); Sara Borjaib, Safat (KW)

(*) Notice: Subject to any disclaimer, the term of this patent is extended or adjusted under 35 U.S.C. 154(b) by 0 days.

(21) Appl. No.: 16/225,526

(22) Filed: Dec. 19, 2018

(51) Int. Cl.
*A61B 5/05* (2006.01)
*A61B 5/00* (2006.01)
*G01N 21/359* (2014.01)
*A61B 5/1455* (2006.01)
*G01N 21/47* (2006.01)

(52) U.S. Cl.
CPC .......... *A61B 5/4504* (2013.01); *A61B 5/0082* (2013.01); *A61B 5/0062* (2013.01); *A61B 5/1455* (2013.01); *G01N 21/359* (2013.01); *G01N 21/4795* (2013.01)

(58) Field of Classification Search
None
See application file for complete search history.

(56) References Cited

U.S. PATENT DOCUMENTS

| 8,792,951 B1 | 7/2014 | Mao et al. | |
|---|---|---|---|
| 9,250,182 B2 | 2/2016 | Gan et al. | |
| 2002/0002336 A1* | 1/2002 | Marchitto | A61B 5/0059 600/473 |

(Continued)

FOREIGN PATENT DOCUMENTS

| WO | 2007097702 A1 | 8/2007 |
|---|---|---|
| WO | 2013070864 A2 | 5/2013 |

OTHER PUBLICATIONS

Sultan et al. "Modeling and tissue parameter extraction challenges for free space broadband fNIR brain imaging systems." Imaging; Manipulation, and Analysis of Biomolecules, Cells, and Tissues IX. vol. 7902. International Society for Optics and Photonics, 2011.

(Continued)

*Primary Examiner* — Jonathan Cwern
(74) *Attorney, Agent, or Firm* — Richard C. Litman

(57) ABSTRACT

The method of detecting bone fractures using backscattered light makes use of backscattered near infrared (NIR) light to determine if a body part of a patient is healthy, has a bone fracture, or has an edema. An incident beam of near infrared light is generated by a light source, and has both an incident amplitude and an incident phase. The incident beam of NIR light is directed toward the patient's body part, and a backscattered beam of NIR light is received from the body part. The backscattered beam of NIR light has a backscattered amplitude and a backscattered phase. The determination of whether the body part is healthy, has a bone fracture or has an edema is made based on the level of absorption of the incident beam of NIR light and/or based on the amount of scattering, based on the phase difference, of the incident beam of NIR light.

12 Claims, 3 Drawing Sheets

(56) References Cited

U.S. PATENT DOCUMENTS

| | | | |
|---|---|---|---|
| 2005/0010130 A1* | 1/2005 | Morris | A61B 5/0059 600/562 |
| 2006/0192965 A1* | 8/2006 | Tromberg | A61B 5/0059 356/432 |
| 2009/0279773 A1 | 11/2009 | Gan et al. | |
| 2012/0203114 A1 | 8/2012 | Bechtel et al. | |

OTHER PUBLICATIONS

Hampson et al. "Near infrared monitoring of human skeletal muscle oxygenation during forearm ischemia." Journal of Applied Physiology 64.6 (1988): 2449-2457.

Shuler et al. "Near-infrared spectroscopy in lower extremity trauma." J Bone Joint Surg Am 91.6 (2009): 1360-1368.

\* cited by examiner

METHOD OF DETECTING BONE FRACTURES USING BACKSCATTERED LIGHT

BACKGROUND

1. Field

The disclosure of the present patent application relates to medical diagnostic tools, and particularly to a method of detecting bone fractures using backscattered, near infrared (NIR) light.

2. Description of the Related Art

X-ray evaluations of injured bones are frequently conducted in hospitals and clinics for the purpose of determining if a bone has been broken in an injury. The vast majority of these evaluations reveal normal bone, and the injury in such cases is labeled as a soft-tissue, usually trivial, injury. In such cases, the X-ray evaluation was unnecessary, resulting in an unnecessary exposure to X-ray radiation, as well as an unnecessary hospital visit and associated costs.

Although portable and relatively inexpensive non-X-ray diagnostic devices, such as ultrasound devices, exist, such devices typically either require expert training in the interpretation of the signal/image or are intended for highly specialized purposes. While ultrasound devices may be useful for their intended applications of providing information about soft tissue structure and function, the characteristics of ultrasound make it unsuitable for high-quality diagnostic images of bone. Thus, medical technology currently uses significantly more expensive, cumbersome, and potentially dangerous test methods, such as X-ray analysis, to identify acute structural changes in bone, such as those that appear in fractures or intrinsic bone lesions.

Although a number of devices that utilize ultrasound or electromagnetic energy to visualize or make determinations about certain properties of skeletal tissue exist, such devices typically do not provide for ease of use or accuracy. Human tissue varies greatly in the distance from skin to the underlying bone, and in the characteristics of the tissues between them. A need therefore exists for a simple, low-cost and portable device which is tolerant of a large degree of variability in user technique, and which is capable of producing a sensitive and specific indication of the likelihood of a fracture in the area of an injury. Thus, a method of detecting bone fractures using backscattered light solving the aforementioned problems is desired.

SUMMARY

The method of detecting bone fractures using backscattered light makes use of backscattered near infrared (NIR) light to determine if a body part of a patient is healthy, has a bone fracture, or has an edema. An incident beam of near infrared light is generated by a light source, such as a multi-wavelength laser or light emitting diode (LEI)) source. The incident beam of near infrared light has both an incident amplitude, $A_I$, and an incident phase, $\phi_I$, associated therewith. The incident beam of near infrared light is directed toward the patient's body part, and a backscattered beam of near infrared light is received from the body part. The backscattered beam of near infrared light also has a backscattered amplitude, $A_{BS}$, and a backscattered phase, $\phi_{BS}$, associated therewith.

The backscattered amplitude and the backscattered phase of the backscattered beam of near infrared light are measured by a network analyzer or the like, allowing an insertion loss and an insertion phase difference to be calculated. The insertion loss, $I_L$, is calculated as $$I_L = 20\log\frac{A_{BS}}{A_I},$$

and the insertion phase difference, $I_{PD}$, is calculated as $I_{PD} = \phi_{BS} - \phi_I$. The determination of the body part being healthy, having a fracture, or having an edema can be based on the calculated insertion loss, the calculated insertion phase difference, or both. It can be determined that the body part of the patient has a bone fracture if the insertion loss is above a first loss threshold (i.e., a relatively high absorption of the incident NIR light beam) and/or the insertion phase difference is below a first phase threshold (i.e., a relatively low percentage of scattering of the incident NIR light beam). If the insertion loss is below a second loss threshold (i.e., a relatively low absorption of the incident NIR light beam) and/or the insertion phase difference is above a second phase threshold (i.e., a relatively high percentage of scattering of the incident NIR light beam), then the body part can be determined to be healthy. It can be determined that the body part of the patient has an edema if the insertion loss is between the first loss threshold and the second loss threshold (i.e., a medium level of absorption of the incident NIR light beam) and/or if the insertion phase difference is between the first phase threshold and the second phase threshold (i.e., a medium level of scattering of the incident NIR light beam).

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
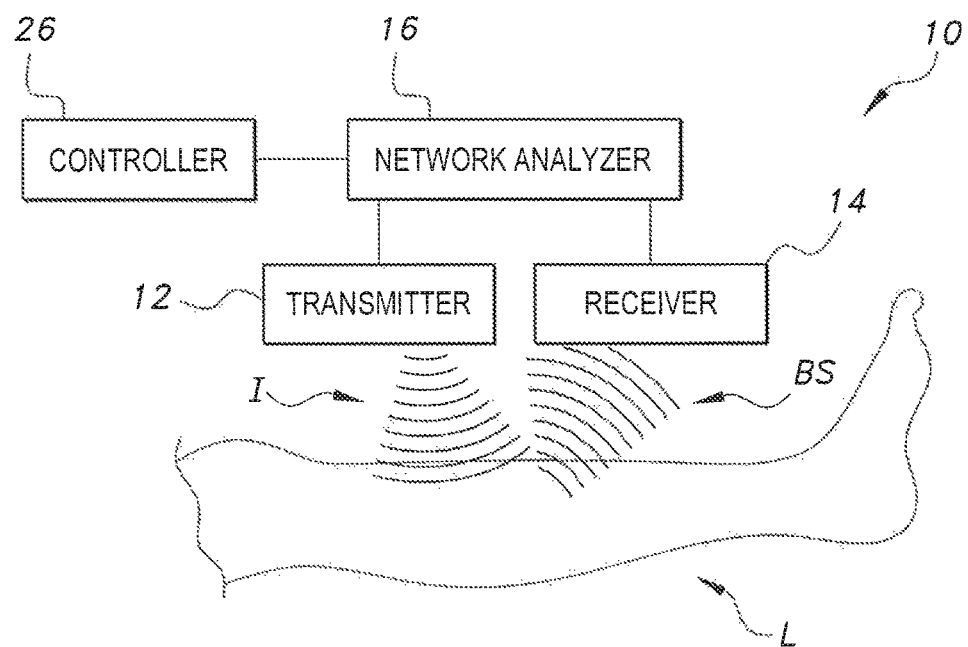
FIG. 1 is a block diagram illustrating a device for implementing a method of detecting bone fractures using backscattered light.

The method of detecting bone fractures using backscattered light makes use of backscattered near infrared (NIR) light to determine if a body part of a patient is healthy, has a bone fracture, or has an edema. As shown in FIG. 1, a device 10 for implementing the method of detecting bone fractures using backscattered light includes a transmitter 12 and a receiver 14. An incident beam of near infrared light I is generated by the transmitter 12 and directed toward the body part of the patient. In FIG. 1, the body part is shown as a patient's leg L, however, it should be understood that leg L is shown in FIG. 1 for exemplary purposes only.

Figure 2:
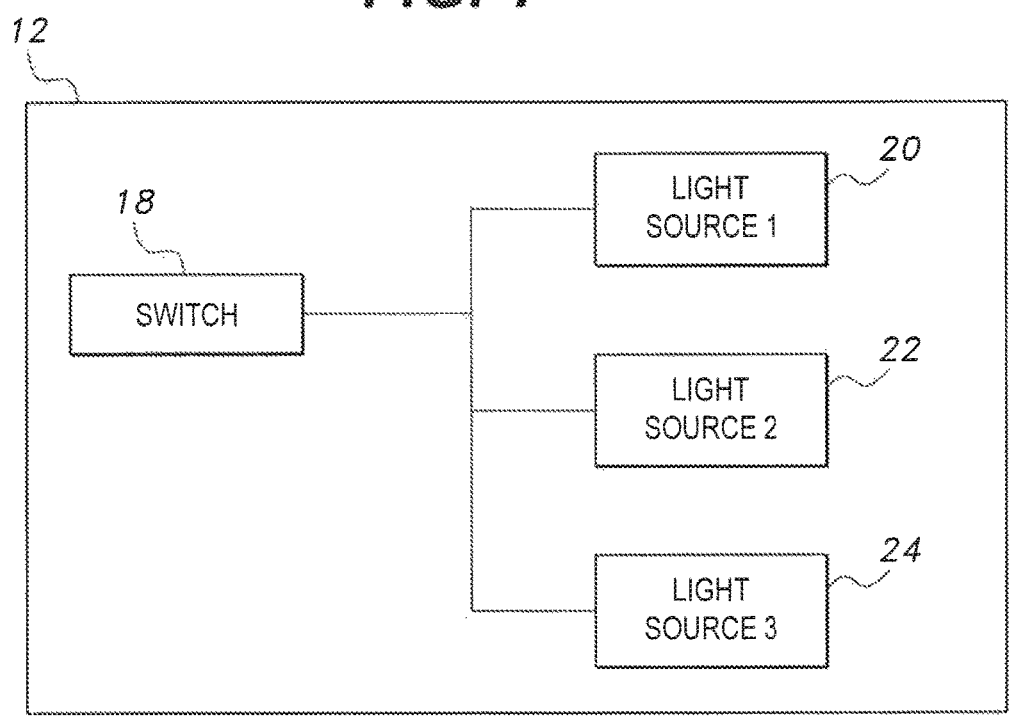
FIG. 2 is a block diagram illustrating a transmitter of the device of FIG. 1.

Transmitter 12 includes a light source for generating the incident beam of near infrared light I. As shown in FIG. 2, the light source may be a multi-wavelength laser or light emitting diode (LED) source. As will be described in greater detail below, in order to test the method of detecting bone fractures using backscattered light, a three-wavelength light source was used. Thus, in the non-limiting example of FIG. 2, first, second and third light sources 20, 22, 24 are shown, which may respectively generate functional near infrared light (fNIR) at wavelengths of 670 nm, 795 nm and 850 nm. These three wavelengths of fNIR have been used for spectroscopic measurements of bone tissue, and can be used to accurately detect levels of oxygenated and deoxygenated hemoglobin using the properties of light absorption and scattering. In testing of the method of detecting bone fractures using backscattered light according to the present teachings, as will be described in greater detail below, the transmitter used was a vertical-cavity surface-emitting laser (VCSEL).

The incident beam of near infrared light I, generated by transmitter 12, has both an incident amplitude, $A_I$, and an incident phase, $\phi_I$, associated therewith. The incident beam of near infrared light I is directed toward the patient's body part (i.e., the patient's leg L in the non-limiting example of FIG. 1), and a backscattered beam of near infrared light BS is received from the body part. The backscattered beam of near infrared light BS also has a backscattered amplitude, $A_{BS}$, and a backscattered phase, $\phi_{BS}$, associated therewith. Receiver 14 may be any suitable type of receiver, such as an avalanche photodiode (APD) detector.

The backscattered amplitude and the backscattered phase of the backscattered beam of near infrared light are measured by a network analyzer 16 or the like, allowing an insertion loss and an insertion phase difference to be calculated. The insertion loss, $I_L$, is calculated as $$I_L = 20\log\frac{A_{BS}}{A_I},$$

and the insertion phase difference, $I_{PD}$, is calculated as $I_{PD}=\phi_{BS}-\phi_I$. As will be described in greater detail below, in testing the method of detecting bone fractures using backscattered light, a network analyzer 16, with a broadband frequency of 30-1000 MHz, was connected to the VCSEL transmitter 12 and the APD receiver 14. The distance between transmitter 12 and receiver 14 was 1.5 cm, although it should be understood that the penetration depth may be increased by decreasing this distance. The calculations may be performed by a controller 26, which may be any suitable type of controller, such as a processor, personal computer, programmable logic controller or the like.

The determination of the body part being healthy, having a fracture, or having an edema can be based on the calculated insertion loss, $I_L$, the calculated insertion phase difference, $I_{PD}$, or both. It can be determined that the body part of the patient has a bone fracture if the insertion loss, $I_L$, is above a first loss threshold (i.e., a relatively high absorption of the incident NIR light beam) and/or the insertion phase difference, $I_{PD}$, is below a first phase threshold (i.e., a relatively low percentage of scattering of the incident NIR light beam). If the insertion loss, $I_L$, is below a second loss threshold (i.e., a relatively low absorption of the incident NIR light beam) and/or the insertion phase difference, $I_{PD}$, is above a second phase threshold (i.e., a relatively high percentage of scattering of the incident NIR light beam), then the body part can be determined to be healthy. It can be determined that the body part of the patient has an edema if the insertion loss, $I_L$, is between the first loss threshold and the second loss threshold (i.e., a medium level of absorption of the incident NIR light beam) and/or if the insertion phase difference, $I_{PD}$, is between the first phase threshold and the second phase threshold (i.e., a medium level of scattering of the incident NIR light beam).

In order to test the method of detecting bone fractures using backscattered light, transmitter 12 was constructed using three vertical cavity semiconductor lasers (VCSELs) 20, 22, 24, and integrated with a single-pull-multiple-through (SPMT) switch 18 to frequency modulate the VCSEILs at multiple wavelengths (i.e., 670 nm, 850 nm and 980 nm). A multi-wavelength VCSEL, module no. V3WLM-002, manufactured by Vixar, Inc., of Minnesota, was used as the transmitter 12. As noted above, an avalanche photodiode (APD) detector was used as receiver 14, particularly an ADP module, model no. C5658, manufactured by Hamamatsu® Photonics K.K. Corporation of Japan. An Anritsu® automatic network analyzer, model MS4623B, manufactured by the Anritsu® Corporation of Japan, was used as the network analyzer 16. Switch 18 was an SP3T radio frequency (RF) switch, model no. HMC245QS16, manufactured by the Hittite® Microwave Corporation of Massachusetts. As discussed above, transmitter 12 receives an input signal from the network analyzer 16 through the switch 18, thus generating incident beam I at a desired wavelength (selected by switch 18).

For purposes of testing, a sheep bone was used to simulate human bone. India ink was used to simulate human blood. A combination of water and the India ink was used to simulate human tissue. A sample of actual human blood was taken for a reference test of its scattering coefficient, allowing for proper calibration of the concentration of India ink in water to simulate human blood and tissue. The reference case (i.e., the "high scattering" case) was considered to be when the amount of Indian ink was equal to the amount of blood in a non-damaged body, where the bone was intact. The "medium scattering" case was considered to be when there was a small fracture in the bone, resulting in an excess amount of blood, resulting in a change in the scattering parameters. The "low scattering" case was considered to be when the bone was broken. In this situation, there is a relatively large quantity of blood, compared to the reference case, which causes much greater absorption of the photons.

Figure 3:
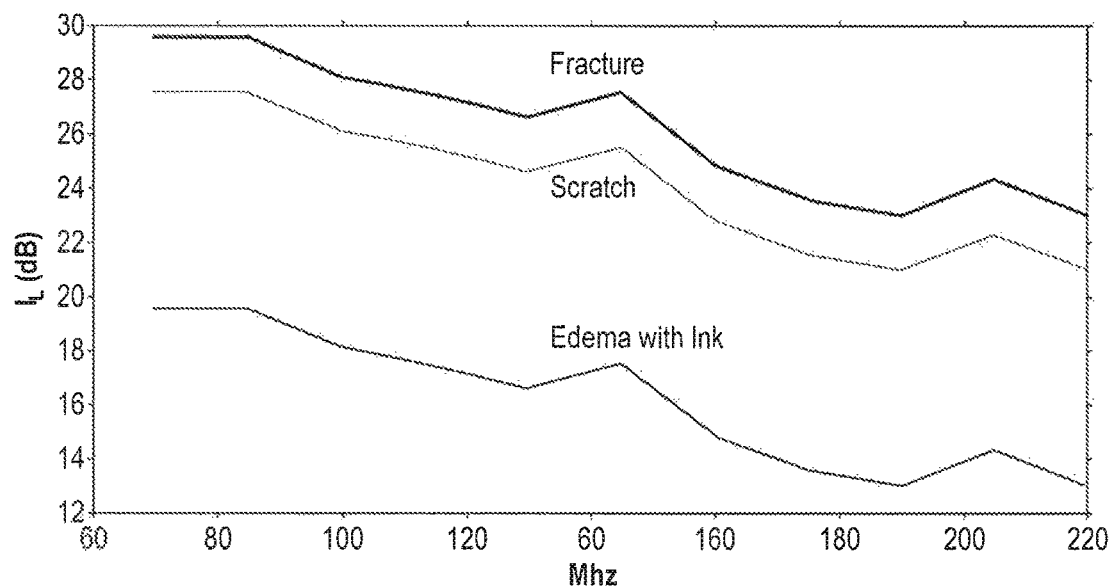
FIG. 3 is a graph comparing insertion loss results for the method of detecting bone fractures using backscattered light for cases including an edema (simulated with India ink), a bone scratch and a bone fracture.
Figure 4:
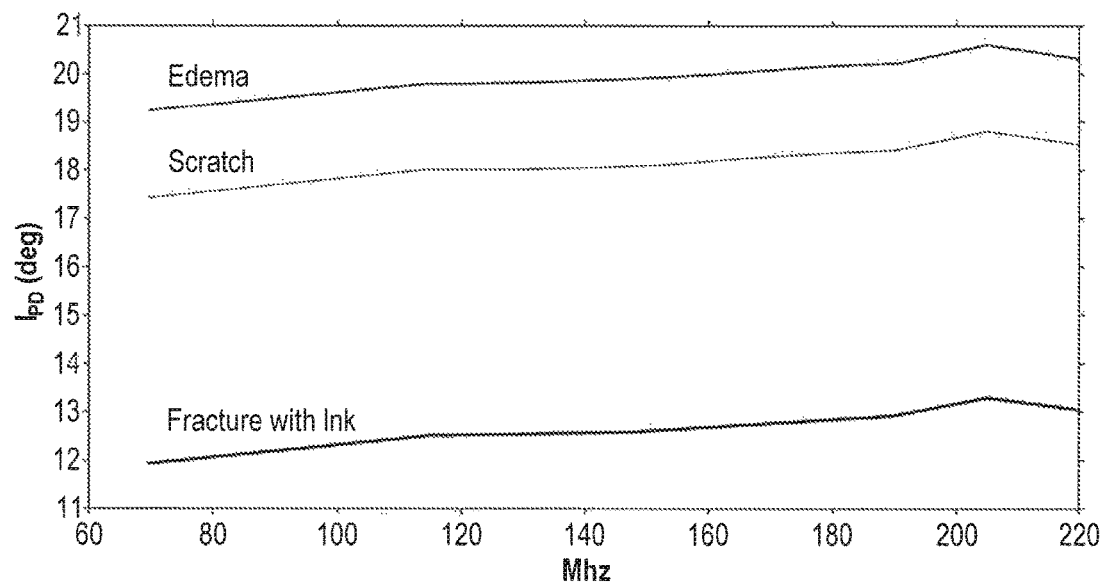
FIG. 4 is a graph comparing insertion phase difference results for the method of detecting bone fractures using backscattered light for cases including an edema, a bone scratch and a bone fracture (simulated with India ink).
Figure 5:
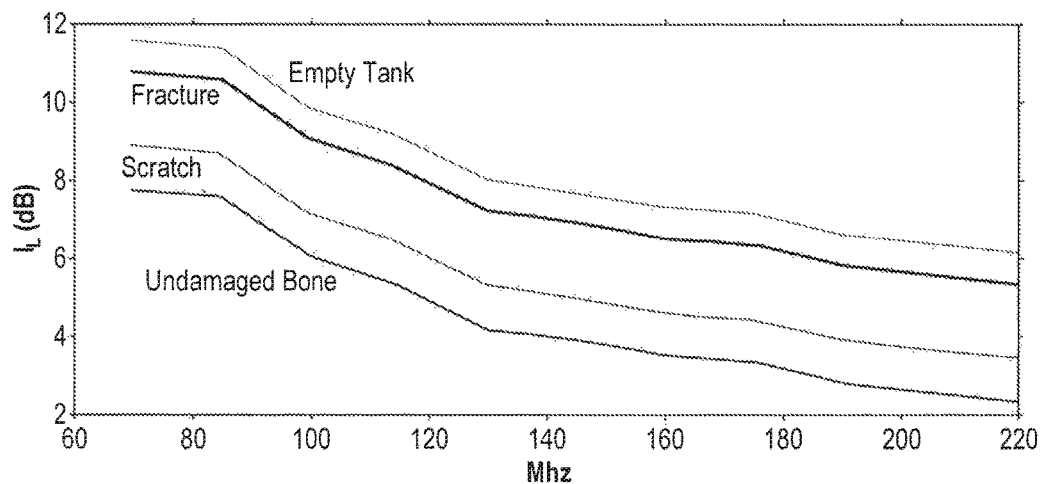
FIG. 5 is a graph comparing insertion loss results for the method of detecting bone fractures using backscattered light, without the usage of India ink, for cases including a healthy undamaged bone, a bone scratch, a bone fracture, and a test case for no bone present.
Figure 6:
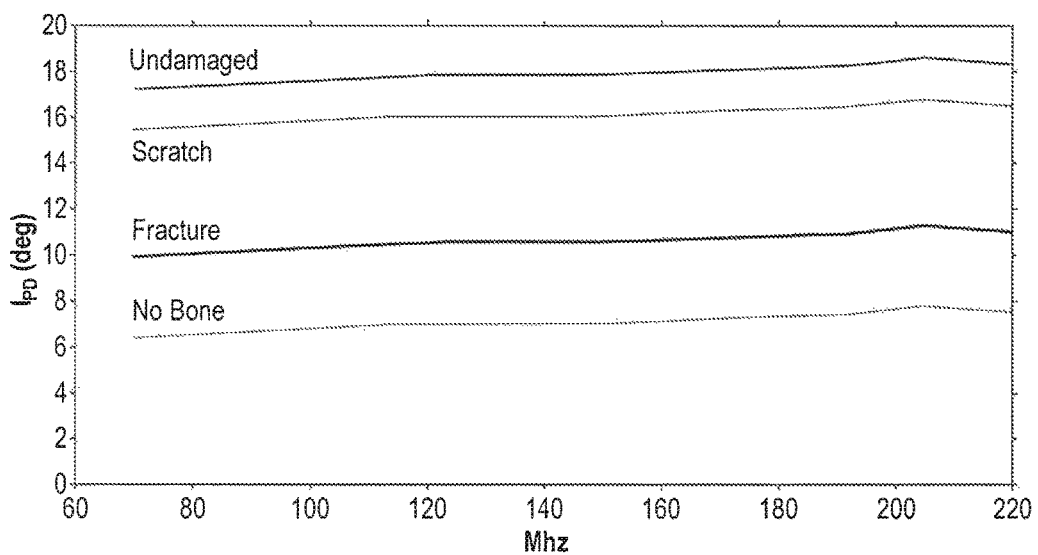
FIG. 6 is a graph comparing insertion phase difference results for the method of detecting bone fractures using backscattered light, without the usage of India ink, for cases including a healthy undamaged bone, a bone scratch, a bone fracture, and a test case for an empty testing tank.

FIG. 3 and FIG. 4 respectively show the results for insertion loss and insertion phase difference. In FIG. 3, it can be seen that the results indicating a bone fracture have the highest insertion loss across the entire frequency range and that the edema (measured with India ink) has the lowest insertion loss across the frequency range. The middle set of data (i.e., between the bone fracture and the edema) represent data from a bone scratch. In FIG. 4, the greatest insertion phase difference is found for the edema, and the lowest insertion phase difference is found for the bone fracture (measured with India ink). Again, the middle set of data (i.e., between the bone fracture and the edema) represent data from the bone scratch. FIGS. 5 and 6 show similar sets of results, but without the addition of India ink. As shown in FIG. 5, without the addition of India ink to simulate blood and tissue, a test case for an empty testing case has the highest insertion loss. From here, the insertion loss decreases, as expected, for the respective cases of a bone fracture, a bone scratch, and a healthy, or undamaged, bone. Similarly, in FIG. 6, the greatest insertion phase difference is found for the healthy, or undamaged, bone. The results respectively decrease for the cases of a bone scratch, a bone fracture, and a test case for no bone present.

Corresponding data is shown below in Tables 1 and 2, respectively showing the data for insertion loss and insertion phase difference. In Tables 1 and 2, cases A7 and A8 represent the data from bone fractures, case A6 represents a bone scratch, cases A2 and A5 represent an edema, and cases A3 and A4 represent a healthy bone. Each data point was averaged ten times for ten measurements.

TABLE 1

Insertion Loss Data (in dB)

| Frequency (Hz) | A2 | A5 | A4 | A3 | A6 | A7 | A8 |
|---|---|---|---|---|---|---|---|
| $6.99 \times 10^7$ | 11.56 | 10.76 | 8.859 | 7.759 | 19.54 | 27.5308 | 29.542 |
| $8.4875 \times 10^7$ | 11.37 | 10.56 | 8.671 | 7.571 | 19.55 | 27.5385 | 29.549 |
| $9.985 \times 10^7$ | 9.835 | 9.034905 | 7.135 | 6.035 | 18.1 | 26.1012 | 28.11 |
| $1.15 \times 10^8$ | 9.12 | 8.3209 | 6.42 | 5.32 | 17.41 | 25.4065 | 27.434 |
| $1.3 \times 10^8$ | 7.9975 | 7.1975 | 5.298 | 4.198 | 16.6 | 24.549 | 26.6102 |
| $1.45 \times 10^8$ | 7.7 | 6.905 | 5 | 3.9 | 17.52 | 25.5198 | 27.5187 |
| $1.6 \times 10^8$ | 7.3 | 6.519 | 4.6 | 3.5 | 14.85 | 22.8439 | 24.8429 |
| $1.75 \times 10^8$ | 7.14 | 6.3324 | 4.44 | 3.34 | 13.57 | 21.5692 | 23.54758 |
| $1.9 \times 10^8$ | 6.6 | 5.813 | 3.9 | 2.8 | 12.99 | 21.02 | 22.9789 |
| $2.05 \times 10^8$ | 6.36 | 5.5595 | 3.66 | 2.56 | 14.31 | 22.324 | 24.3049 |
| $2.2 \times 10^8$ | 6.12 | 5.3423 | 3.92 | 2.32 | 13.04 | 21.105 | 23.06 |

TABLE 2

Insertion Phase Difference Data (in degrees)

| Frequency (Hz) | A2 | A5 | A4 | A3 | A6 | A7 | A8 |
|---|---|---|---|---|---|---|---|
| $6.99 \times 10^7$ | 6.463 | 9.959 | 15.461 | 17.258 | 11.93 | 17.463 | 19.265 |
| $8.4875 \times 10^7$ | 6.646 | 10.143 | 15.644 | 17.432 | 12.1346 | 17.651 | 19.441 |
| $9.985 \times 10^7$ | 6.835 | 10.324 | 15.832 | 17.637 | 12.346 | 17.841 | 19.639 |
| $1.15 \times 10^8$ | 7.015 | 10.523 | 16.013 | 17.84 | 12.515 | 18.019 | 19.825 |
| $1.3 \times 10^8$ | 7.051 | 10.545 | 16.047 | 17.854 | 12.551 | 18.051 | 19.8701 |
| $1.45 \times 10^8$ | 7.068 | 10.559 | 16.062 | 17.868 | 12.572 | 18.068 | 19.8702 |
| $1.6 \times 10^8$ | 7.188 | 10.682 | 16.181 | 17.99 | 12.69 | 18.191 | 19.981 |
| $1.75 \times 10^8$ | 7.342 | 10.832 | 16.34 | 18.14 | 12.851 | 18.334 | 20.151 |
| $1.9 \times 10^8$ | 7.421 | 10.931 | 16.422 | 18.2265 | 12.9209 | 18.4245 | 20.225 |
| $2.05 \times 10^8$ | 7.813 | 11.311 | 16.82 | 18.6106 | 13.3205 | 18.82068 | 20.619 |
| $2.2 \times 10^8$ | 7.545 | 11.035 | 16.541 | 18.3314 | 13.045 | 18.55013 | 20.345 |

It is to be understood that the method of detecting bone fractures using backscattered light is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of detecting bone fractures using backscattered light, comprising the steps of:
    generating an incident beam of near infrared light having an incident amplitude, $A_I$, and an incident phase, $\phi_I$, associated therewith;
    directing the incident beam of near infrared light toward a body part of a patient;
    receiving a backscattered beam of near infrared light from the body part of the patient, the backscattered beam of near infrared light having a backscattered amplitude, $A_{BS}$, and a backscattered phase, $\phi_{BS}$, associated therewith;
    measuring the backscattered amplitude and the backscattered phase of the backscattered beam of near infrared light;
    calculating an insertion loss, $I_L$, as $$I_L = 20\log\frac{A_{BS}}{A_I};$$

calculating an insertion phase difference, $I_{PD}$, as $I_{PD} = \phi_{BS} - \phi_I$; and
    determining that the body part of the patient has a bone fracture if the insertion loss is above a first loss threshold and the insertion phase difference is below a first phase threshold, thereby determining that the body part of the patient is healthy if the insertion loss is below a second loss threshold and the insertion phase difference is above a second phase threshold, and determining that the body part of the patient has an edema if the insertion loss is between the first loss threshold and the second loss threshold, and if the insertion phase difference is between the first phase threshold and the second phase threshold.

2. The method of detecting bone fractures using backscattered light according to claim 1, wherein the incident beam of near infrared light is generated using first, second and third light sources.

3. The method of detecting bone fractures using backscattered light according to claim 2, wherein the first, second, and third light sources generate functional near infrared light at wavelengths of 670 nm, 795 nm, and 850 nm, respectively.

4. The method of detecting bone fractures using backscattered light according to claim 1, wherein the incident beam of near infrared light is generated using a vertical-cavity surface-emitting laser.

5. A method of detecting bone fractures using backscattered light, comprising the steps of:
    generating an incident beam of near infrared light having an incident amplitude, A_I, associated therewith;
    directing the incident beam of near infrared light toward a body part of a patient;
    receiving a backscattered beam of near infrared light from the body part of the patient, the backscattered beam of near infrared light having a backscattered amplitude, A_BS, associated therewith;

measuring the backscattered amplitude of the backscattered beam of near infrared light;

calculating an insertion loss, $I_L$, as $$I_L = 20\log\frac{A_{BS}}{A_I};$$

and determining that the body part of the patient has a bone fracture if the insertion loss is above a first loss threshold, thereby determining that the body part of the patient is healthy if the insertion loss is below a second loss threshold, and determining that the body part of the patient has an edema if the insertion loss is between the first loss threshold and the second loss threshold.

6. The method of detecting bone fractures using backscattered light according to claim 5, wherein the incident beam of near infrared light is generated using first, second and third light sources.

7. The method of detecting bone fractures using backscattered light according to claim 6, wherein the first, second, and third light sources generate functional near infrared light at wavelengths of 670 nm, 795 nm, and 850 nm, respectively.

8. The method of detecting bone fractures using backscattered light according to claim 5, wherein the incident beam of near infrared light is generated using a vertical-cavity surface-emitting laser.

9. A method of detecting bone fractures using backscattered light, comprising the steps of:

generating an incident beam of near infrared light having an incident phase, $\phi_I$, associated therewith;

directing the incident beam of near infrared light toward a body part of a patient;

receiving a backscattered beam of near infrared light from the body part of the patient, the backscattered beam of near infrared light having a backscattered phase, $\phi_{BS}$, associated therewith;

measuring the backscattered phase of the backscattered beam of near infrared light;

calculating an insertion phase difference, $I_{PD}$, as $I_{PD} = \phi_{BS} - \phi_I$; and determining that the body part of the patient has a bone fracture if the insertion phase difference is below a first phase threshold, thereby determining that the body part of the patient is healthy if the insertion phase difference is above a second phase threshold, and determining that the body part of the patient has an edema if the insertion phase difference is between the first phase threshold and the second phase threshold.

10. The method of detecting bone fractures using backscattered light according to claim 9, wherein the incident beam of near infrared light is generated using first, second and third light sources.

11. The method of detecting bone fractures using backscattered light according to claim 10, wherein the first, second, and third light sources generate functional near infrared light at wavelengths of 670 nm, 795 nm, and 850 nm, respectively.

12. The method of detecting bone fractures using backscattered light according to claim 9, wherein the incident beam of near infrared light is generated using a vertical-cavity surface-emitting laser.

* * * * *